Aug. 12, 1941. K. SAWADA Plant Pat. 481
CAMELLIA PLANT
Filed March 17, 1941
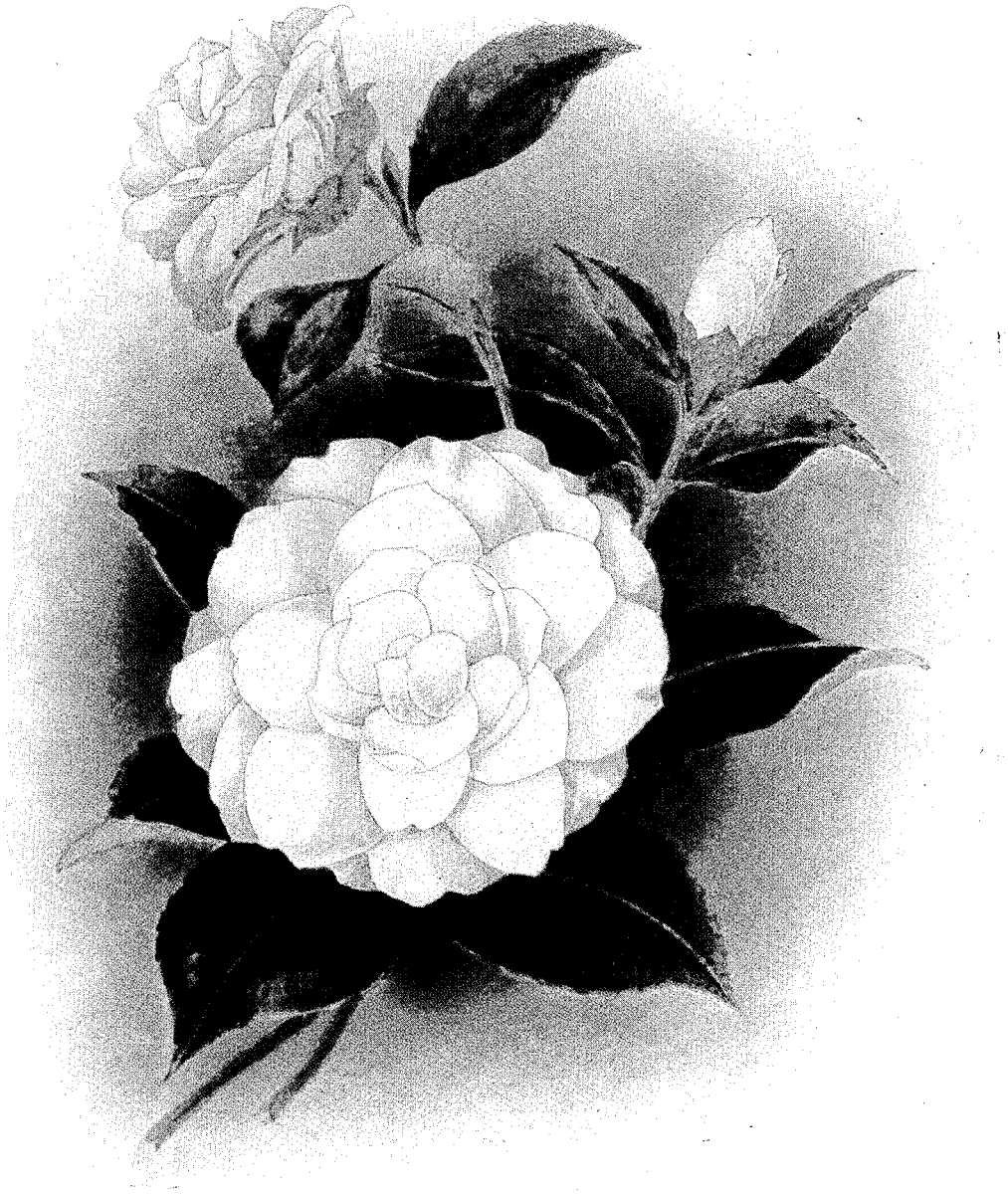
Witness
Addison E. Avery
Inventor
Kosaku Sawada
By Rummler, Rummler & Davis
Attys.

Patented Aug. 12, 1941

Plant Pat. 481

UNITED STATES PATENT OFFICE

481

CAMELLIA PLANT

Kosaku Sawada, Crichton, Ala., assignor to Overlook Nurseries, Crichton, Ala., a partnership composed of said Sawada and S. Imura Application March 17, 1941, Serial No. 383,758

1 Claim. (Cl. 47—60)

The present discovery relates to a new and distinct variety of pink *camellia japonica* and is the result of definite breeding efforts carried on since 1925. The purpose of the hybridization was to produce a very double, light pink camellia whose buds would not drop off (this being a common occurrence with the double varieties), and which would be superior to other varieties for outdoor growing. It is a seedling of Nobillissima, the pollen parent being unknown.

This new variety is exceptionally vigorous in its growth and freely produces large flowers borne mostly singly on long and slender stems. The color of the open camellia is a delicate or faint shade of pink. The flower is of rose form, full, double and imbricated. The tree which is about fifteen years old is now 7 feet in height and 4 feet in width. The lasting quality of these blossoms is exceptionally good; as a cut flower at least a week, and on the plant from ten days to two weeks. The resistance of this new variety to heat and cold is quite remarkable. It has withstood freezing weather and summer heat.

The plant has been asexually reproduced for several generations by cutting and grafting and all the improved characters of this new variety have been thoroughly established and remain true.

The original illustrations accompanying this application show in approximately true colors three specimens of this new variety in various stages of opening.

Following is a detailed description of this variety:

*Blossom*

Size: 3–3½ inches in diameter—sometimes reaches 4 inches.
Form: Rose form, full, double, imbricated.
Borne: Mostly singly.
Stems: Long and slender.
Petalage: 70 to 100, large petals, measure 1½ inches to 1¾ inches long; 1¼ inches in width.
Color: Delicate shade of pink.
Texture: Very fine.
Not affected by either wet or hot weather.
Blooms January to February.
Appearance: Somewhat like gardenia flowers.

*Bud*

Size: ¾ inch long, ½ inch wide (in proportion).
Form: Round to oblong.
Sepals: 5, orbicular.
No genital organs.
Lasting quality, on plant: 10 days to 2 weeks; as cut flower: at least a week.

*Plant*

Upright grower, very compact.
Height: A 15-year old tree is now 7 feet in height; and 4 feet wide.
Foliage: Abundant in quantity.
*Color.*—New foliage—a shade of light green, old foliage—a shade of very dark green with large veins.
Size of leaf: Average: 3½ inches in length; 1½ to 1¾ inches in width.
Texture: Medium thickness, also lightly serrated.
Disease resistance: Very strong.
Shape of leaf: Oblong-lanceolate to ovate-lanceolate.

The colors of this improved camellia when compared with a Dictionary of Color by Maerz & Paul are as follows:

| Section | Color | Plate | Letter | No. |
|---|---|---|---|---|
| Flower: | | | | |
| Body of flower (outer petals). | | 1 | A | 1 |
| Blending with | | 1 | B | 1 |
| Center section | | 1 | A | 2 |
| Deep center | Opera Pink | 1 | B | 8 |
| Under side of blossoms | | 3 | C | 2 |
| Bud: | | | | |
| Body of petal | | 10 | E | 1 |
| Tipped with | Peach Blossom | 1 | C | 2 |
| Calyx | Bister Green | 13 | L | 5 |
| Edged with | Alamo+ | 14 | A | 12 |
| Leaf: | | | | |
| Body of leaf | | 24 | E | 10 |
| Vein | Art Green | 22 | L | 7 |
| Under side of leaf | Courge Green | 21 | L | 3 |
| Stem | Olive Wood | 15 | E | 10 |

By careful comparison, when grown under comparable conditions, this new variety most nearly resembles the well-known "Lady Humes' Blush," there appearing to be slight difference in the shape of the flower, the size, color, time of blooming, keeping quality and size of foliage.

However, there are several important differences which indicate the distinctions of the present variety; namely: number of petals of the flower (70 to 100); excellent quality for outdoor blooming shrub; shape, texture and color of the foliage; growth and shape of bush—this camellia bush is upright with slender branches, very compact and a vigorous grower—while the "Lady Humes' Blush" is spread somewhat with rather coarse branches, not compact, and a very slow grower. This camellia is propagated very easily both from cutting and grafting, while the "Lady Humes' Blush" is hard to propagate, especially by cutting. This camellia has exceptional resistant power against cold and heat, has withstood the freeze of winter and the heat of summer. The "Lady Humes' Blush" has poor resistance; it freezes easily and gets sun-burned in the summertime.

The delicate pink color of this flower, together with its size, ease of propagation, upright compact growth, fine texture, superior keeping qualities and resistance to disease and weather conditions combine to provide a very desirable and exquisite product. One of the chief characteristics of the plant is its fine quality for outdoor blooming. It is much superior to any other camellia for cut flower purposes.

Having thus disclosed my invention, I claim:

A new and distinct variety of camellia plant, substantially as shown and described, characterized particularly by its vigorous upright, compact, fast growth; long stems; fine foliage; resistance to disease and weather conditions; fine quality for outdoor blooming; ease of propagation; superior keeping qualities; the delicate pink color and finer texture of the flowers; and its superiority over other varieties of camellias for cut flower purposes.

KOSAKU SAWADA.